US011542215B2

(12) United States Patent
Veige et al.

(10) Patent No.: US 11,542,215 B2
(45) Date of Patent: Jan. 3, 2023

(54) REMOVING ACETYLENE FROM ETHYLENE GAS STREAMS DURING POLYETHYLENE SYNTHESIS

(71) Applicant: UNIVERSITY OF FLORIDA RESEARCH FOUNDATION, INCORPORATED, Gainesville, FL (US)

(72) Inventors: Adam S. Veige, Gainesville, FL (US); Brent S. Sumerlin, Gainesville, FL (US); Zhihui Miao, Gainesville, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 279 days.

(21) Appl. No.: 17/032,663

(22) Filed: Sep. 25, 2020

(65) Prior Publication Data

US 2021/0094896 A1    Apr. 1, 2021

Related U.S. Application Data

(60) Provisional application No. 62/907,059, filed on Sep. 27, 2019.

(51) Int. Cl.
*C07C 7/177* (2006.01)
*B01D 53/86* (2006.01)
*C08F 110/02* (2006.01)

(52) U.S. Cl.
CPC ............ *C07C 7/177* (2013.01); *B01D 53/864* (2013.01); *C08F 110/02* (2013.01); *B01D 2255/20776* (2013.01)

(58) Field of Classification Search
None
See application file for complete search history.

(56) References Cited

U.S. PATENT DOCUMENTS 3,086,066 A * 4/1963 Breiter .................... C07C 7/177
585/854
9,206,266 B2 * 12/2015 Veige .................. C08F 4/62082

FOREIGN PATENT DOCUMENTS

CN      101658761 A      3/2010
CN      109622000 A      4/2019

OTHER PUBLICATIONS

Roland et al., "Cyclic polymers from alkynes", Nature Chemistry, Macmillan Publishers Limited, vol. 8, 2016, pp. 791-796. (Year: 2016).*
Osswald et al., Palladium Gallium Intermetallic Compounds for the Selective Hydrogenation of Acetylene Part II: Surface Characterization and Catalytic Performance, Journal of Catalysis, 258: 219-227 (2008).

* cited by examiner

*Primary Examiner* — Philip Y Louie
(74) *Attorney, Agent, or Firm* — Marshall, Gerstein & Borun LLP

(57) ABSTRACT

Disclosed herein are methods for removing acetylene from an ethylene gas stream wherein a catalyst reacts with the acetylene to polymerize said acetylene forming an ethylene gas stream substantially free of acetylene.

20 Claims, No Drawings

REMOVING ACETYLENE FROM ETHYLENE GAS STREAMS DURING POLYETHYLENE SYNTHESIS

CROSS-REFERENCE TO RELATED APPLICATIONS

This application claims the benefit under 35 U.S.C. § 119(e) of U.S. Provisional Patent Application No. 62/907,059, filed on Sep. 27, 2019, the entirety of which is hereby incorporated by reference.

STATEMENT REGARDING FEDERALLY SPONSORED RESEARCH OR DEVELOPMENT

This invention was made with U.S. government support under CHE1565654 and 1808234 awarded by the National Science Foundation. The U.S. government has certain rights in the invention.

BACKGROUND

The production of polyethylene from ethylene gas is an important industrial process. Acetylene is a common impurity in ethylene feeds and can act a poison to catalysts in the reaction of ethylene to polyethylene. Most commonly, acetylene is removed via hydrogenation. However, economic efficiency requires high selectivity of the acetylene hydrogenation in the presence of an excess of ethylene to prevent the hydrogenation reaction of ethylene to ethane, thereby killing the reactant. Known catalysts that promote the hydrogenation reaction of acetylene exhibit activity but possess limited selectivity and stability. Therefore, there is a need for catalysts that can react with acetylene selectively in the presence of excess ethylene producing a pure ethylene feed.

SUMMARY

Provided herein are methods of removing acetylene from an ethylene gas stream comprising contacting the gas stream with a catalyst such that the catalyst reacts with acetylene to polymerize the acetylene thereby forming an ethylene gas stream substantially free of acetylene; wherein the catalyst has a structure of

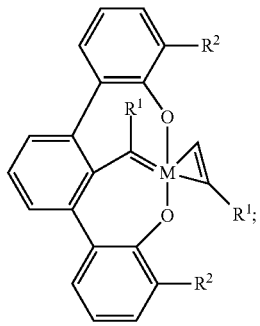

each $R^1$ is independently $Ar^1$, $C_1$-$C_{22}$ alkyl, or $(R^3)_3$—Si—; each $R^2$ is independently $Ar^1$, $C_3$-$C_{22}$ alkyl, or $(R^3)_3$—Si—; M is W or Mo; $Ar^1$ is aryl or heteroaryl which can be optionally substituted, wherein the heteroaryl is a 5-12 membered aromatic ring comprising from 1 to 4 heteroatoms selected from O, N, and S, and the optional substitutions are 1 to 3 groups independently selected from halo, $C_{1-6}$ alkyl, $OC_{1-6}$alkyl, and $C_{1-6}$haloalkyl; each occurrence of $R^3$ is independently $C_1$-$C_{22}$ alkyl, $Ar^1$, —O—($C_1$-$C_{22}$ alkyl), —O—$Ar^1$, —N—($C_1$-$C_{22})_2$ alkyl, or —N—$Ar^1_2$; and L is absent or a neutral ligand.

In some embodiments, each $R^1$ is $C_{1-22}$alkyl. In embodiments, at least one $R^1$ is t-butyl. In some cases, each $R^1$ is t-butyl. In embodiments, at least one $R^1$ is $Ar^1$. In some embodiments, at least one $R^1$ is phenyl.

In embodiments, each $R^2$ is $C_1$-$C_6$ alkyl. In some embodiments, each $R^2$ is t-butyl.

In embodiments, L is absent. In some cases, L is a neutral ligand. In some embodiments, L is tetrahydrofuran, $Et_2O$, thiophene, or pyridine. In embodiments, L is tetrahydrofuran.

In embodiments, M is W.

In embodiments, the catalyst is in a solution. In some embodiments, the gas stream is bubbled through the solution. In some cases, the ethylene gas stream substantially free of acetylene comprises less than 1% by weight acetylene. In embodiments, ethylene gas stream substantially free of acetylene comprises less than 0.5% by weight acetylene.

In some embodiments, the acetylene is polymerized at room temperature. In embodiments, the acetylene is polymerized at atmospheric pressure.

In embodiments, the methods herein further comprise reacting the ethylene gas stream substantially free of acetylene under polymerization conditions to form polyethylene.

DETAILED DESCRIPTION

Many modifications and other embodiments will come to mind to one skilled in the art to which the disclosed compositions and methods pertain having the benefit of the teachings presented herein. Therefore, it is to be understood that the disclosures are not to be limited to the specific embodiments disclosed and that modifications and other embodiments are intended to be included within the scope of the appended claims.

Disclosed herein are methods of removing acetylene from an ethylene gas stream comprising contacting the gas stream with a catalyst such that the catalyst reacts with acetylene to polymerize the acetylene thereby form an ethylene gas stream substantially free of acetylene. The catalyst used in the disclosed methods has a structure of

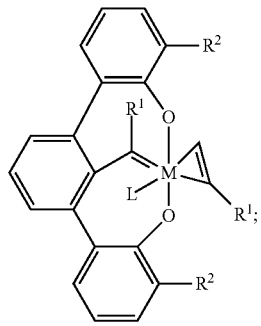

each $R^1$ is independently $Ar^1$, $C_1$-$C_{22}$ alkyl, or $(R^3)_3$—Si—; each $R^2$ is independently $Ar^1$, $C_3$-$C_{22}$ alkyl, or $(R^3)_3$—Si—; M is W or Mo; $Ar^1$ is aryl or heteroaryl which can be optionally substituted, wherein the heteroaryl is a 5-12 membered aromatic ring comprising from 1 to 4 heteroatoms selected from O, N, and S, and the optional substitutions are 1 to 3 groups independently selected from halo, $C_{1-6}$ alkyl, $OC_{1-6}$alkyl, and $C_{1-6}$haloalkyl; each occurrence of $R^3$ is independently $C_1$-$C_{22}$ alkyl, $Ar^1$, —O—($C_1$-$C_{22}$ alkyl), —O—$Ar^1$, —N—($C_1$-$C_{22}$)$_2$ alkyl, or —N—$Ar^1_2$; and L is absent or a neutral ligand.

As used herein, and unless specified otherwise, the term "alkyl" refers to straight or branched chain hydrocarbyl groups including from 1 to 22 carbon atoms. For instance, an alkyl can have from 1 to 20 carbon atoms, 2 to 20 carbon atoms, 2 to 10 carbon atoms, 3 to 5 carbon atoms, or 4 to 8 carbon atoms. The term $C_n$ means that the alkyl group has "n" carbon atoms. For example, $C_4$ alkyl refers to an alkyl group that has 4 carbon atoms. $C_{3-22}$alkyl refers to an alkyl group having a number of carbon atoms encompassing the entire range (i.e., 3 to 22 carbon atoms), as well as all subgroups (e.g., 3-20, 4-11, 3-10, 5-9, 6-8, 3, 4, 5, 6, 7, 8, 9, 10, 11, 12, 13, 14, 15, 16, 17, 18, 19, 20, 21, and 22 carbon atoms). Exemplary alkyls include straight chain alkyl groups such as methyl, ethyl, propyl, butyl, pentyl, hexyl, heptyl, octyl, nonyl, decyl, undecyl, dodecyl, tridecyl, tetradecyl, and the like, and also include branched chain isomers of straight chain alkyl groups. Thus, alkyl groups include primary alkyl groups, secondary alkyl groups, and tertiary alkyl groups.

As used herein, the term "aryl" refers to monocyclic or polycyclic (e.g., fused bicyclic and fused tricyclic) carbocyclic aromatic ring systems. Examples of aryl groups include, but are not limited to, phenyl, tolyl, naphthyl, tetrahydronaphthyl, phenanthrenyl, biphenylenyl, indanyl, indenyl, anthracenyl, and fluorenyl. Unless otherwise indicated, an aryl group can be an unsubstituted aryl group or a substituted aryl group. Some contemplated substitutions include 1 to 3 groups independently selected from halo, $C_{1-6}$ alkyl, $OC_{1-6}$ alkyl, and $C_{1-6}$haloalkyl.

As used herein, the term "heteroaryl" refers to a cyclic aromatic ring having five to twelve total ring atoms (e.g., a monocyclic aromatic ring with 5-6 total ring atoms), and containing one to four ring heteroatoms selected from nitrogen, oxygen, and sulfur. Unless otherwise indicated, a heteroaryl group can be unsubstituted or substituted with one or more groups, and in particular one to four or one to three. In some cases, the heteroaryl group is substituted with one to three groups independently selected from halo, $C_{1-6}$ alkyl, $OC_{1-6}$ alkyl, and $C_{1-6}$haloalkyl. Heteroaryl groups can be isolated (e.g., pyridyl) or fused to another heteroaryl group (e.g., purinyl), a cycloalkyl group (e.g., tetrahydroquinolinyl), a heterocycloalkyl group (e.g., dihydronaphthyridinyl), and/or an aryl group (e.g., benzothiazolyl and quinolyl). Examples of heteroaryl groups include, but are not limited to, thienyl, furyl, pyridyl, pyrrolyl, oxazolyl, quinolyl, thiophenyl, isoquinolyl, indolyl, triazinyl, triazolyl, isothiazolyl, isoxazolyl, imidazolyl, benzothiazolyl, pyrazinyl, pyrimidinyl, thiazolyl, and thiadiazolyl. When a heteroaryl group is fused to another heteroaryl group, then each ring can contain five or six total ring atoms and one to three heteroatoms in its aromatic ring.

As used herein, the term "halo" is defined as fluoro, chloro, bromo, and iodo. The term "haloalkyl" refers to an alkyl group that is substituted with at least one halogen, and includes perhalogenated alkyl (i.e., all hydrogen atoms substituted with halogen).

As used herein, the term "neutral ligand" refers to an L-type ligand. L-type ligands are described in detail in Gray L. Spessard and Gary L. Miessler, Organometallic Chemistry, published by Oxford University Press, 2010, for example, page 59. In embodiments, L can comprise $N(R^3)_3$, $Ar^1$, $R^3OR^3$, $P(R^3)_3$, $R^3CHO$, $R^3COR^3$, $R^3COOR^3$, and $S(R^3)_2$. In embodiments, L can be $N(R^3)_3$, $P(R^3)_3$, $Ar^1$, $S(R^3)_2$ or $R^3OR^3$. In some cases, L can be selected from the group comprising diethyl ether, methyl tert-butyl ether (MTBE), diisopropyl ether, tetrahydrofuran (THF), dioxane and the like. In embodiments, L can be pyridine or derivatives thereof, such as, N,N-dimethylaminopyridine. In embodiments, L can comprise tetrahydrofuran or substituted tetrahydrofuran, pyridine or substituted pyridine, or thiophene or substituted thiophene.

In general, $R^1$ is independently $Ar^1$, $C_1$-$C_{22}$ alkyl, or $(R^3)_3$—Si—. In some cases, each $R^1$ can be an alkyl group such as methyl, ethyl, n-propyl, i-propyl, n-butyl, i-butyl, t-butyl, or a larger alkyl group, for example $C_5$ to $C_{20}$ alkyl. In embodiments, each $R^1$ is independently $C_1$-$C_6$ alkyl. In embodiments, each $R^1$ is t-butyl. In embodiments, each $R^1$ is independently $Ar^1$. In general, $Ar^1$ is a $C_6$-$C_{22}$ aryl or 5-12 membered heteroaryl group comprising 1 to 4 ring heteroatoms selected from O, N, and S, and the optional substitutions are 1 to 3 groups independently selected from halo, $C_{1-6}$ alkyl, $OC_{1-6}$alkyl, and $C_{1-6}$haloalkyl. In some cases, $Ar^1$ comprises pyrrolyl, furanyl, thiophenyl, imidazolyl, pyrazolyl, oxazolyl, isoxazolyl, thiazolyl, phenyl, tolyl, pyridinyl, pyrazinyl, pyrimidinyl, pyridazinyl, or triazinyl. $Ar^1$ can also be a fused aryl or heteroaryl group, including, but not limited to, benzofuranyl, isobenzofuranyl, indolyl, isoindolyl, benzothiophenyl, bensimidazolyl, purinyl, indazolyl, benzoxazolyl, benzisoxazolyl, benzothiazolyl, naphthalenyl, anthracenyl, quinolinyl, isoquinolinyl, quinoxalinyl, acridinyl, quinazolinyl, cinnolinyl, and phthalazinyl. In embodiments, each $R^1$ is a phenyl or tolyl.

In embodiments, at least one $R^1$ comprises $C_1$-$C_6$ alkyl. In refinements of the foregoing embodiment, the at least one $R^1$ comprises t-butyl. In refinements of the foregoing embodiment, the at least one $R^1$ comprises methyl, ethyl, or isopropyl. In embodiments, at least one $R^1$ comprises $Ar^1$. In refinements of the foregoing embodiment, the at least one $R^1$ comprises phenyl or tolyl.

In general, $R^2$ is independently $Ar^1$, $C_3$-$C_{22}$ alkyl, or $(R^3)_3$—Si—. In some cases, each $R^2$ can be an alkyl group such as n-propyl, isopropyl, n-butyl, i-butyl, t-butyl, or a larger alkyl group, for example $C_5$ to $C_{20}$ alkyl. In embodiments, each $R^2$ is independently $C_3$-$C_6$ alkyl. In embodiments, each $R^2$ is t-butyl. In embodiments, each $R^2$ is isopropyl. In embodiments, at least one $R^2$ is $Ar^1$. In embodiments, each $R^2$ is independently $Ar^1$. In embodiments, at least one $R^1$ is phenyl or tolyl. In some cases, each $R^2$ is a phenyl or tolyl.

In embodiments, at least one $R^2$ comprises $C_3$-$C_6$ alkyl. In some embodiments, at least one $R^2$ comprises t-butyl. In some embodiments, at least one $R^2$ comprises isopropyl. In embodiments, at least one $R^2$ comprises $Ar^1$. In some embodiments, at least one $R^2$ comprises phenyl or tolyl.

In general, each occurrence of $R^3$ is independently $C_1$-$C_{22}$ alkyl, $Ar^1$, —O—($C_1$-$C_{22}$ alkyl), —O—$Ar^1$, —N—($C_1$-$C_{22}$)$_2$ alkyl, or —N—$Ar^1_2$. In embodiments, each $R^3$ can be an alkyl group such as n-propyl, isopropyl, n-butyl, i-butyl, t-butyl, or a larger alkyl group, for example $C_5$ to $C_{20}$ alkyl. In embodiments, each $R^3$ can be selected from $C_1$-$C_6$ alkyl. In embodiments, each $R^3$ is methyl or ethyl. In embodiments, each $R^3$ is isopropyl. In embodiments, each $R^3$ can be $Ar^1$. In embodiments, at least one $R^1$ is phenyl or tolyl. In some embodiments, each $R^1$ is a phenyl or tolyl.

In embodiments, at least one $R^3$ comprises $C_1$-$C_6$ alkyl. In some embodiments, at least one $R^3$ comprises methyl or ethyl. In some embodiments, at least one $R^3$ comprises isopropyl. In embodiments, at least one $R^3$ comprises $Ar^1$. In some embodiments, at least one $R^3$ is phenyl or tolyl.

In general, M is W or Mo. In embodiments, M is W.

In embodiments, the catalyst is

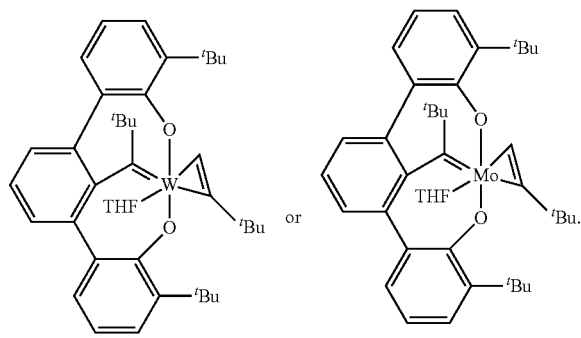

The catalyst as described herein can polymerize acetylene selectively in the presence of ethylene. In embodiments, the catalyst does not react with ethylene. It is advantageous to have a catalyst, such as the catalysts described herein, selectively react with acetylene but not with ethylene, as this can provides ethylene gas that is substantially free of acetylene.

The methods disclosed herein can comprise contacting the ethylene gas stream, contaminated with acetylene, with a catalyst as disclosed herein such that the catalyst reacts with the acetylene to polymerize the acetylene thereby forming an ethylene gas stream substantially free of acetylene. The term "substantially free of acetylene" refers to the ethylene gas stream having less than 5% by weight acetylene. In embodiments, the ethylene gas stream substantially free of acetylene can comprise less than 5% by weight acetylene, or less than 4% by weight acetylene, or less than 3% by weight acetylene, or less than 2% by weight acetylene, or less than 1% by weight acetylene, or less than 0.5% by weight acetylene, or less than 0.1% by weight acetylene, or up to 5% by weight acetylene, or up to 4% by weight acetylene, or up to 3% by weight acetylene, or up to 2% by weight acetylene, or up to 1% by weight acetylene, or up to 0.5% by weight acetylene, or up to 0.1% by weight acetylene.

The methods disclosed herein can comprise a catalyst loading of up to 20 mol %. In embodiments, the catalyst loading can be up to 10 mol %, 9 mol %, 8 mol %, 7 mol %, 6 mol %, 5 mol %, 4 mol %, 3 mol %, 2 mol %, 1 mol %, 0.5 mol %, 0.1 mol %, 0.01 mol %, or 0.001 mol %.

In embodiments, the ethylene gas stream, before contacting with the catalyst, can comprise up to 95% by weight acetylene. In some embodiments, the ethylene gas stream can comprise acetylene in a range of 0.1% to 95% by weight, or 1% to 75% by weight, or 50% to 75% by weight, or 1% to 50% by weight, or 5% to 40% by weight, or 0.1% to 30% by weight, or 1% to 20% by weight, or 0.01% to 10% by weight, such as 0.1%, 0.5%, 1%, 2%, 5%, 10%, 20%, 30%, 40%, 50%, 75% and 95% by weight.

The methods disclosed herein can comprise the catalyst in solution. The solution can comprise a solvent. Examples of solvents that may be used in the polymerization reaction include organic solvents that are inert under the polymerization conditions, such as aromatic hydrocarbons, halogenated hydrocarbons, ethers, aliphatic hydrocarbons, or mixtures thereof. In embodiments, the solvent can be benzene, toluene, xylenes, pentane, hexane, methyl t-butyl ether, heptane, 1,4 dioxane, diethyl ether, 1,2 dichloroethane, or a combination thereof. In embodiments, the solution can comprise a deuterated solvent. When the catalyst is in solution, the disclosed methods allow for purified ethylene in a facile manner as well as recyclable use of catalyst, because the polyacetylene formed is insoluble in the solution and precipitates out, allowing for ease of purification and reuse of the catalyst.

In embodiments, the gas stream is bubbled through a solution of the catalyst such that the catalyst reacts with acetylene to polymerize the acetylene thereby forming an ethylene gas stream substantially free of acetylene.

The methods as described herein can include reaction temperatures in a range of about −80° C. to about 100° C., about −70 to about 80° C., about −50° C. to about 75° C., about −25° C. to about 50° C., about 0° C. to about 35° C., about 5° C. to about 30° C., about 10° C. to about 25° C., about 15° C. to about 25° C., or about 20° C. to about 25° C., for example, about 0° C., about 5° C., about 10° C., about 15° C., about 20° C., about 25° C., about 30° C., or about 35° C. In embodiments, the temperature can be room temperature. Reaction times can be instantaneous or in a range of about 30 seconds to about 72 h, about 1 min to about 72 h, about 5 min to about 72 h, about 10 min to about 48 h, about 15 min to about 24 h, about 20 min to about 12 h, about 25 min to about 6 h, or about 30 min to about 3 h, for example, 30 seconds, 1 min, 5 min, 10 min, 15 min, 20 min, 25 min, 30 min, 35 min, 40 min, 45 min, 50 min, 55 min, 60 min, 75 min, 90 min, 105 min, 2 h, 3 h, 4 h, 5 h, 6 h, 12 h, 18 h, 24 h, 36 h, 48 h, 60 h, or 72 h.

The methods can be carried out at, for example, ambient temperatures in dry conditions under an inert atmosphere. In embodiments, the inert atmosphere can comprise $N_2$ or Ar.

The methods as described herein can be carried out at any suitable temperature to one of skill in the art. In embodiments, the methods can be carried out at atmospheric pressure. In embodiments, the methods can be carried out at pressures of up to 15 psi, for example, 1 psi, 5 psi, 6 psi, 7 psi, 8 psi, 9 psi, 10 psi, 11 psi, 12 psi, 13 psi, 14 psi, or 15 psi, or in a range of 1 psi to 10 psi, or 1 psi to 5 psi, or 5 psi to 15 psi, or 10 psi to 15 psi.

The disclosure herein provides methods of removing acetylene from an ethylene gas stream, wherein the catalyst reacts with acetylene selectively without reacting with ethylene. In embodiments, the catalyst polymerizes acetylene producing a polyacetylene. The reaction of the catalyst with acetylene to produce polyacetylene can be advantageous, as the polyacetylene is extremely insoluble and can be separated out of the reaction readily. Therefore the purity of both the catalyst and the ethylene gas stream are improved. In embodiments, the polyacetylene produced by the reaction of the catalyst with the acetylene in the ethylene gas stream can be cyclic.

In embodiments, the method can further comprise the ethylene gas stream substantially free of acetylene being further reacted under polymerization conditions to form polyethylene.

EXAMPLES

Gas stream purification and preparation—Ethylene gas was passed through a cold trap packed with drierite that removed moisture. Acetylene gas was passed through a cold trap packed with activated carbon and drierite followed by a column packed with layers of drierite, activated carbon, and 3 Å sieves. Both purified gases were bubbled into deuterated benzene ($C_6D_6$) for 3 minutes. This provided the acetylene/$C_6D_6$ and ethylene/$C_6D_6$ solutions, respectively.

Acetylene Reaction in the presence of ethylene—Two sealable NMR tubes were charged with a 200 µL of the acetylene/$C_6D_6$ solution and 140 µL of the ethylene/$C_6D_6$ solution. Into one of the acetylene/ethylene/$C_6D_6$ solution was added 10.0 μL of a $C_6D_6$ solution of 1 (10 mg/mL). Upon addition of 1 the solution turned dark blue/black with black precipitates formed on the wall of the tube. As a control, an addition of 10.0 μL of a blank $C_6D_6$ solution to the second NMR tube did not result in any observable physical changes. The $^1$H NMR spectrum of the tube without catalyst 1 revealed the ratio of dissolved acetylene and ethylene in the initial mixture solution was 2:1, where acetylene protons resonated at 1.34 ppm and ethylene protons resonated at 5.25 ppm. The integrations of acetylene and ethylene relative to $C_6D_6$ was 53% and 25%, respectively. The $^1$H NMR of the solution with the addition of 1 indicated the catalyst consumed all the acetylene monomer, as the resonance at 1.34 ppm completely disappeared. However, the ethylene concentration stayed constant at 25% relative to $C_6D_6$. The resulting polyacetylene that forms does not appear in the $^1$H NMR spectrum since it is insoluble. This indicated that catalyst 1 selectively polymerizes acetylene in an acetylene/ethylene mixture solution. It also indicates it can remove acetylene to below the detection limit of the NMR. The catalyst (1) used has a structure of

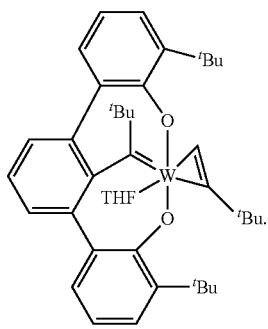

(I)

Control Experiment: Only ethylene—Two sealable NMR tubes were charged with 400 μL of pure ethylene/$C_6D_6$ solutions. To the tubes were added a 20.0 μL $C_6D_6$ solution of 1 (10 mg/mL) and 20.0 μL of a blank $C_6D_6$ solution, respectively. Upon addition of 1 the solution turns slightly yellow due to the color of the complex. The $^1$H NMR spectrum of the tube without catalyst 1 revealed the integration of dissolved ethylene to $C_6D_6$ is 23%. The $^1$H NMR spectra of the tube after 15 min, 1 h, and 24 h of the addition of 1 revealed that the ethylene concentration remained constant (~22% relative to $C_6D_6$). The comparison of the $^1$H NMR spectrum of 1 and ethylene mixed with 1 after 1 h, the resonance from 1 at 11.65, 1.67, 12.4, and 0.96 ppm stayed unchanged in the mixture of ethylene and 1, indicating 1 does not polymerize ethylene.

What is claimed:
1. A method of removing acetylene from an ethylene gas stream comprising
contacting the gas stream with a catalyst such that the catalyst reacts with acetylene to polymerize the acetylene thereby forming an ethylene gas stream substantially free of acetylene;
wherein
the catalyst has a structure of

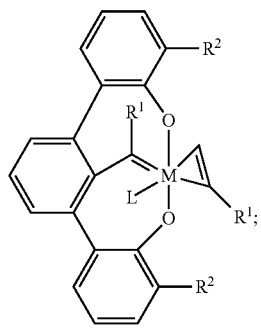

each $R^1$ is independently $Ar^1$, $C_1$-$C_{22}$ alkyl, or $(R^3)_3$—Si—;
each $R^2$ is independently $Ar^1$, $C_3$-$C_{22}$ alkyl, or $(R^3)_3$—Si—;
M is W or Mo;
$Ar^1$ is aryl or heteroaryl which can be optionally substituted, wherein the heteroaryl is a 5-12 membered aromatic ring comprising from 1 to 4 heteroatoms selected from O, N, and S, and the optional substitutions are 1 to 3 groups independently selected from halo, $C_{1-6}$ alkyl, $OC_{1-6}$alkyl, and $C_{1-6}$haloalkyl;
each occurrence of $R^3$ is independently $C_1$-$C_{22}$ alkyl, $Ar^1$, —O—($C_1$-$C_{22}$ alkyl), —O—$Ar^1$, —N—($C_1$-$C_{22}$)$_2$ alkyl, or —N—$Ar^1_2$; and
L is absent or a neutral ligand.
2. The method of claim 1, wherein each $R^1$ is $C_{1-22}$ alkyl.
3. The method of claim 2, wherein at least one $R^1$ is t-butyl.
4. The method of claim 3, wherein each $R^1$ is t-butyl.
5. The method of claim 1, wherein at least one $R^1$ is $Ar^1$.
6. The method of claim 5, wherein at least one $R^1$ is phenyl.
7. The method of claim 1, wherein each $R^2$ is $C_1$-$C_6$ alkyl.
8. The method of claim 7, wherein each $R^2$ is t-butyl.
9. The method of claim 1, wherein L is absent.
10. The method of claim 1, wherein L is a neutral ligand.
11. The method of claim 10, wherein L is tetrahydrofuran, $Et_2O$, thiophene, or pyridine.
12. The method of claim 11, wherein L is tetrahydrofuran.
13. The method of claim 1, wherein M is W.
14. The method of claim 1, wherein the catalyst is in a solution.
15. The method of claim 14, wherein the gas stream is bubbled through the solution.
16. The method of claim 1, wherein the ethylene gas stream substantially free of acetylene comprises less than 1% by weight acetylene.
17. The method of claim 16, wherein the ethylene gas stream substantially free of acetylene comprises less than 0.5% by weight acetylene.
18. The method of claim 1, wherein the acetylene is polymerized at room temperature.
19. The method of claim 1, wherein the acetylene is polymerized at atmospheric pressure.
20. The method of claim 1, further comprising reacting the ethylene gas stream substantially free of acetylene under polymerization conditions to form polyethylene.

* * * * *